(12) United States Patent
Moore

(10) Patent No.: US 9,217,009 B2
(45) Date of Patent: *Dec. 22, 2015

(54) VERSION OF FDG DETECTABLE BY SINGLE-PHOTON EMISSION COMPUTED TOMOGRAPHY

(71) Applicant: MALLINCKRODT LLC, Hazelwood, MO (US)

(72) Inventor: Dennis A. Moore, Ferguson, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/478,154

(22) Filed: Sep. 5, 2014

(65) Prior Publication Data
US 2014/0378677 A1    Dec. 25, 2014

Related U.S. Application Data

(63) Continuation of application No. 13/120,537, filed as application No. PCT/US2009/058379 on Sep. 25, 2009, now Pat. No. 8,858,916.

(60) Provisional application No. 61/194,782, filed on Sep. 30, 2008.

(51) Int. Cl.
| C07H 15/26 | (2006.01) |
| C07H 15/12 | (2006.01) |
| A61K 49/00 | (2006.01) |
| A61K 51/04 | (2006.01) |

(52) U.S. Cl.
CPC ............ *C07H 15/26* (2013.01); *A61K 49/0002* (2013.01); *A61K 51/048* (2013.01); *A61K 51/0482* (2013.01); *A61K 51/0491* (2013.01); *C07H 15/12* (2013.01)

(58) Field of Classification Search
None
See application file for complete search history.

(56) References Cited

U.S. PATENT DOCUMENTS

| 5,807,879 | A * | 9/1998 | Rosebrough ................. 514/387 |
| 8,758,723 | B2 | 6/2014 | Yang |
| 8,858,916 | B2 | 10/2014 | Moore |
| 2007/0248537 | A1 | 10/2007 | Yang |

FOREIGN PATENT DOCUMENTS

| CA | 2738786 A1 | 4/2010 |
| EP | 2341944 | 7/2011 |
| JP | 2012504131 A | 2/2012 |
| WO | 200170724 A1 | 9/2001 |
| WO | 200177140 A2 | 10/2001 |
| WO | 03091232 A2 | 11/2003 |
| WO | 2005058829 A1 | 6/2005 |
| WO | 2005076011 A2 | 8/2005 |
| WO | 2005117931 A2 | 12/2005 |
| WO | 2006026855 A1 | 3/2006 |
| WO | 2010039609 A2 | 4/2010 |

OTHER PUBLICATIONS

Holland et al. Functionalized bis(thiosemicarbazonato) complexes of zinc and copper: synthetic platforms toward site-specific radiopharmaceuticals. 2007 Inorg. Chem. 46: 465-485.*
Petrig et al. Derivatization of glucose and 2-deoxyglucose for transition metal complexation: substitution reactions with organometallic 99mTc and Re precursors and fundamental NMR investigations. 2001 Chemistry 7: 1868-1873.*
Ferreira, Carbohydrate-appended 3-hydroxy-4-pyridinoe complexes of the [M(CO)3]+ core (M=Re, 99mTc, 186Re), 2006, Bioconjug. Chem. 17:1321-1329.
Aller, Flow cytometric analysis of glucose transport by rat brain cells, Cytometry, 1997, 27:262-268.
Basak, Synthesis of conjugates of L-fucose and ortho-carborane as potential agents for boron neutron capture therapy, Can. J. Chem., 2002, 80:943-948.
Bayly, Carbohydrate Conjugates for Molecular Imaging and . . . , Bioconjugate Chem., 2004, 15:923-926.
Chen, Synthesis and biological evaluation of technetium-99m-labeled deoxyglucose . . . , Bioorganic & Medicinal Chemistry Letters, 2006, 16:5503-5506.
Omichi, Differentiation of Novel Human a-Amylase from Salivary and Pancreatic a-Amylases, 1991, 38(2):193-196.
Dimitrov, Membrane electroporation—fast molecular exchange by electroosmosis, Biochimica et Biophysica Aceta., 1990, 1022:381-392.
Dumas, Versatile Routes to C-2 and C-6 Functionalized . . . , J. Org. Chem., 2003, 68:512.
Ferreira, Glucosamine Conjugates of Tricarbonylcyclopentadienyl Rhenium(I) and Technetium(I) Cores, Inorg. Chem., 2006 45:6979-6987.
Halmos, Synthesis of glucose-chlorambucil derivatives and their recognition by the human GLUT1 glucose transporter, European Journal of Pharmacology, 1996, 318:477-484.
Hayasaki, Quenching Effect of Blood on Fluorescent Glucose Analogue NBDG, Acta Histochem. Cytochem., 1996, 29(3)207-213.
Jonas, N-Acetyl-D-glucosamine countertransport in lysosomal membrane vesicles, Biochem. J., 1990, 268:41-45.
Komor, Sugar specificity and sugar-proton interaction for the hexose-proton-symport system of Chlorella, Eur. J. biochem., 1985, 146:649-656.
May, Selective labeling of the Erythrocyte Hexose Carrier with a Maleimide Derivative of Glucosamine: Relationship of an Exofacial Sulfydryl to Carrier Conformation and Structure, Biochemistry, 1989, 28:1718-1725.

(Continued)

*Primary Examiner* — Michael G Hartley
*Assistant Examiner* — Jennifer Lamberski

(57) ABSTRACT

A compound comprising a metal chelate linked to a hexose carrier for use as a metallopharmaceutical diagnostic or therapeutic agent is provided. The compound is suitable for imaging by single-photon emission computed tomography, computer assisted tomography, magnetic resonance spectroscopy, magnetic resonance imaging, positron emission tomography, fluorescence imaging or x-ray.

12 Claims, No Drawings

(56) References Cited

OTHER PUBLICATIONS

May Jr., Synthesis and Biological Activity of Potential Antimetabolites of L-Fucose, Journal of Medicinal Chemistry, 1979, 22(8):971-976.

Porras, Glutamate Mediates Acute Glucose Transport Inhibition in Hippocampal Neurons, J. of Neuroscience, 2004, 24(43)9669-9673.

Ramjeesingh, Potential affinity and photoaffinity reagents for the membrane protein of human erythrocytes . . . , Can. J. Chem., 1997, 55:3717-3720.

Rauchman, Expression of GLUT-2 Cdna in human B lymphocytes . . . , Biochimica et Biophysica Acta, 1992, 1111:231-238.

Schibli, Synthesis and in Vitro characterization of Organometallic Rhenium and Technetium . . . , Bioconjugate Chem., 2005, 16:105-112.

Shanahan, Photoaffinity Labeling of the Human Erythrocyte . . . , Journal of Biological Chemistry, 1985, 260 (2):10897-10900.

Speizer, Differences between Human and Goose Erythrocytes in Response to . . . , Cancer Research, 1987, 47:4830-4834.

Speizer, Asymmetric transport of a fluorescent glucose analogue by human erythrocytes, Biochimica et biophysica Acta, 1985, 815:75-84.

Spiegel, Use of Nonaqueous Solvents in Parenteral Products, J. Pharmaceutical Sciences, 1963, 52(1):917-927.

Storr, A gluosamine-dipicolylamine conjugate of . . . Dalton Trans., 2005, 654-655.

Weber, Characterization of a photosensitive glucose derivative. A photoaffinity reagent for the erythrocyte hexose transporter, Biochimica et biophysica Acta, 1985, 812:503-511.

Petrig, Derivatization of glucose and 2-deoxyglucose for transition metal complexation: substitution reactions with organometallic 99mTc and Re precursors and fundamental NMR investigations, 2001, Chem. Eur. J., 7:1868-1873.

Notice of Allowance dated Jun. 9, 2014 from related U.S. Appl. No. 13/120,537, 8 pgs.

Final Rejection dated Mar. 21, 2014 from related U.S. Appl. No. 13/120,537, 11 pgs.

Non-Final Rejection dated Mar. 21, 2014 from related U.S. Appl. No. 13/120,537, 11 pgs.

Final Official Action dated Feb. 3, 2015 from related JP application No. 2011-529259, 7 pgs.

Office Action dated Sep. 18, 2014 from related EP application No. 09736724.7.

International Search Report and Written Opinion dated Jul. 23, 2010 from related international application No. PCT/US2009/058379, 9 pgs.

\* cited by examiner

VERSION OF FDG DETECTABLE BY SINGLE-PHOTON EMISSION COMPUTED TOMOGRAPHY

CROSS-REFERENCE TO RELATED APPLICATIONS

This application is a continuation application of U.S. patent application Ser. No. 13/120,537, filed Mar. 23, 2011, which is a U.S. National Stage application of PCT International Patent Application No. PCT/US2009/058379, filed Sep. 25, 2009, which claims the benefit of U.S. Provisional Application Ser. No. 61/194,782, filed Sep. 30, 2008, the contents of each is hereby incorporated by reference in its entirety.

FIELD OF THE INVENTION

The present invention is generally directed to a metal chelate linked to a hexose carrier for use as a metallopharmaceutical diagnostic or therapeutic agent.

BACKGROUND OF THE INVENTION

The rate of glucose metabolism by a living cell is known to be a useful indicator of a variety of abnormal physiological conditions, particularly in human patients. Included among these conditions are various forms of cancer, coronary artery disease, brain tumors and epilepsy. The diagnosis and locale determination of these conditions has been made possible by sophisticated imaging techniques that identify cells which are demonstrating abnormally high or low rates of glucose intake.

Until now, glucose imaging has been performed by positron-emission tomography (PET) with glucose analogs such as carbon-11-labeled glucose and $^{18}$F-labeled 2-deoxy-2-fluoro-D-glucose and its isomer $^{18}$F-labeled 3-deoxy-3-fluoro-D-glucose (collectively referred to as "FDG"). FDG, upon administration to the patient prior to the imaging procedure, enters the cell in the same manner as glucose. For instance, it is believed, without being bound to any particular theory, that FDG and glucose are transported through the cell membrane by glucose transporters Glut 1 and Glut 3. Both FDG and glucose are subsequently phosphorylated at the 6-position by hexokinase thereby forming D-glucose-6-phosphate and 2-deoxy-2-[$^{18}$F]fluoro-D-glucose, respectfully. However, where D-glucose-6-phosphate is a substrate for the phosphohexose isomerase step in the metabolic pathway, 2-deoxy-2-[$^{18}$F]fluoro-D-glucose does not complete the metabolic cycle inside the cells, and therefore accumulates and remains in the cells long enough for imaging to take place. The accumulation and the resulting whole body distribution of FDG as detected by the PET imaging procedure is an indicator of the stage and locus of the abnormality. PET is the imaging technique of choice because it is sensitive enough to usefully detect the annihilation photons emitted by FDG. Other imaging techniques, such as single-photon emission computed tomography (SPECT), do not have the sensitivity required to detect FDG.

Unfortunately, PET is one of the more costly imaging procedures. As a result, nuclear medicine scanning based on glucose transport abnormalities has enjoyed only limited use, and is feasible only at locations where PET equipment is available. This has hindered the development of glucose transport both as a research tool and as a diagnostic method.

As an alternative to FDG, it would be a significant advance in the art to develop a bioavailable glucose derivative that is labeled with a metal that is detectable by non-PET imaging methods.

Schibli, et al., disclose the preparation of glucose linked at the C-2, C-3, C-4 or C-6 sites with an ether (i.e., —O—) linkage to a complex consisting of $^{99m}$technetium or rhenium and a metal coordinating moiety selected from ethyleneiminodiacetic acid, propyleneiminodiacetic acid, octyleneiminodiacetic acid, ethylenepicolylamine mono acetic acid, ethylene histidyl and ethylenebisimidazolyl amino methane. No appreciable uptake of the glucose compounds was observed. See Schibli, et al., "Synthesis and in Vitro Characterization of Organometallic Rhenium and Technetium Glucose Complexes against Glut 1 and Hexokinase", Bioconjugate Chem. 2005, 16, 105-112.

There is a need for glucose imaging compounds that exhibit cellular uptake, are not significantly metabolized in the cell, and that can be detected and quantified by imaging techniques other than PET.

SUMMARY OF THE INVENTION

According to one aspect of the invention, a metallopharmaceutical hexose derivative compound is provided wherein hexose positions C-1, C-2, C-3, C-4 and C-6 are independently substituted with hydrogen, hydroxyl, halogen, hydrocarbyl, substituted hydrocarbyl, or a metal containing moiety. The metal containing moiety comprises a linker and a metal complex comprising a metal coordinating moiety and one or more metal ions. The linker comprises nitrogen, sulfur, or phosphorus, and the metal coordinating moiety is DOTA, DTPA, or IDA. At least one of the C-1, C-2, C-3, C-4 and C-6 substituents is the metal containing moiety. Where C-2 is the metal containing moiety, at least one of C-1, C-3, C-4 and C-6 is hydrogen, halogen, hydrocarbyl, substituted hydrocarbyl, or the metal containing moiety. Where $R_5$ is the metal containing moiety and the metal coordinating moiety is DOTA, the linker is other than a secondary amine.

Still another aspect of the invention is directed to a pharmaceutical formulation comprising the metallopharmaceutical hexose derivative compound wherein the formulation is suitable for administration as an imaging enhancing agent and the compound is present is an amount sufficient to enhance a single-photon emission computed tomography (SPECT) image, a computer assisted tomography (CAT) image, a magnetic resonance spectroscopy (MRS) image, a magnetic resonance imaging (MRI) image, a positron emission tomography (PET) image, a fluorescence image (FI) applicable or an x-ray (XR) image.

Other objects and features will be in part apparent and in part pointed out hereinafter.

DETAILED DESCRIPTION OF THE INVENTION

The present invention provides metallopharmaceutical compounds having a hexose carrier useful for the treatment and/or diagnosis of disease. The compounds exhibit cellular uptake comparable to glucose, and accumulate and remain in the cells long enough for imaging by single-photon emission computed tomography (SPECT), computer assisted tomography (CAT), magnetic resonance spectroscopy (MRS), magnetic resonance imaging (MRI), positron emission tomography (PET), fluorescence imaging (FI) or x-ray (XR) to take place.

Generally, the compounds of the present invention are conjugates represented by formula (1) and comprise three components: a hexose carrier; a metal complex comprising a metal coordinating moiety and a metal; and a linker that binds the metal complex to the hexose.

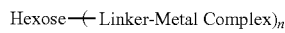
(1)

In formula (1), n is from 1 to 5 and -(linker-metal complex) substitution can occur independently at one or more of hexose positions C-2, C-3, C-4, C-5 and C-6.

The transport mechanism for cellular uptake of the compounds of the present invention is not completely understood. It is believed however that transport is mediated by the family of glucose transporters (GLUTs) that, in humans, contain at least 14 members (SLC1A1-14, GLUT1-14). Various GLUT transporters have been demonstrated to transport a variety of sugars (glucose, 2-deoxyglucose, galactose, fructose, inositol) and sugar analogs (dehydroascorbate, glucosamine, and fluorodeoxyglucose). Transport is bidirectional, allowing transport either into or out of the cell depending on the substrate gradients.

It is believed that the cellular uptake and discharge of the compounds of the present invention is done by the GLUT family of transporters. The present compounds are taken up by hyper-metabolic cancer cells in greater quantity than by normal cells. It has been discovered that a linker that is both a hydrogen donor and a hydrogen acceptor enables uptake of the compounds of the present invention into cells. It has been further discovered that compounds of the present invention containing such a linker are not significantly metabolized inside the cells and therefore accumulate and remain in the cells long enough for imaging to take place. Such compounds do not deposit metals in the cells and are efficiently excreted from the body. It has yet been further discovered that (a) linkers that are not both a hydrogen donor and a hydrogen acceptor, such as oxygen, and (b) metal coordinating moieties that are linked by a ketone to an amine linker, thereby forming an amide (—N—C(O)—) bond are not suitable for the practice of the present invention. The presence of such linkers and/or bonds is believed to inhibit cellular uptake and/or result in metabolism of the compound in the cell causing cleavage of the linker-metal complex from the hexose carrier and accumulation and retention of the cleaved linker-metal complex in the cell.

In one embodiment, the linker is selected from nitrogen, sulfur and phosphorus and is independently selected from the following formulae (1a) to (1e):

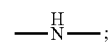
(1a)

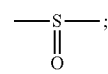
(1b)

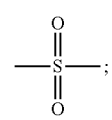
(1c)

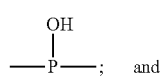
(1d)

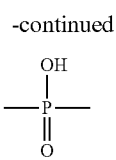
(1e)

In one embodiment, the compound is of formula (2) having a secondary amine linker

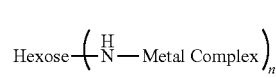
(2)

wherein n is from 1 to 5 and —(NH-metal complex) substitution can occur independently at one or more of hexose positions C-1, C-2, C-3, C-4 and C-6. In another embodiment, n is 2 and the hexose is substituted at any two of hexose positions C-1, C-2, C-3, C-4 and C-6, such as C-2 and C-6. In yet another embodiment, n is 1 and the hexose is substituted at C-2. In still another embodiment, n is 1 and the hexose is substituted at C-6.

Suitable hexoses include glucose, galactose and mannose. The scope of the present invention includes both the α and β hexose isomers as well as the dextrorotatory (D-) and levortatory (L-) hexose isomers. In one embodiment, the hexose is α-D-glucose.

Substituted hexoses of the present are represented by formula (3)

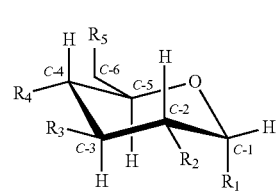
(3)

Any of hexose positions C-1 ($R_1$), C-2 ($R_2$), C-3 ($R_3$), C-4 ($R_4$) and C-6 ($R_5$) that are not substituted by the -(linker-metal complex) moiety can comprise hydrogen and/or hydroxyl or may be substituted with, for example, hydrocarbyl, substituted hydrocarbyl, halogen, nitro, amino, amido, thio or phospho. In another embodiment, the hexose may be substituted with, for example, alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: oxo, hydroxyl, carboxyl, carboxamide, nitro, ether, ketone, amino, ammonium, sulfonate, sulfonamide, terpyridyl, caboxymethylamino, phosphonate, and phosphonamide. In one embodiment, $R_1$, $R_2$, $R_3$, $R_4$ and $R_5$ are independently hydrogen, hydroxyl, halogen, hydrocarbyl, substituted hydrocarbyl, or a linker-metal complex moiety of formula —$R_6$—$R_7R_8$ wherein $R_6$ is a linking group that is both a hydrogen donor and a hydrogen acceptor, $R_7$ comprises a metal coordinating moiety, and $R_8$ comprises one or more metal ions, but wherein at least one of $R_1$, $R_2$, $R_3$, $R_4$ and $R_5$ is a linker-metal complex moiety. When $R_2$ is a linker-metal complex moiety, at least one of $R_1$, $R_3$, $R_4$ and $R_5$ is selected from hydrogen, halogen, hydrocarbyl, substituted hydrocarbyl, and a linker-metal complex moiety.

Any metal capable of detection by SPECT, CAT, MRS, MRI, PET, FI or XR is suitable for the practice of the present invention. Metals suitable for the compounds of the present invention can be selected from the group consisting of aluminum, antimony, arsenic, barium, beryllium, bismuth, cadmium, calcium, cerium, cesium, chromium, cobalt, copper, dysprosium, erbium, europium, gadolinium, gallium, gold, hafnium, holmium, indium, iron, krypton, lanthanum, lead, magnesium, manganese, mercury, molybdenum, neodymium, neptunium, nickel, niobium, osmium, palladium, platinum, plutonium, praseodymium, promethium, protactinium, radium, rhenium, rhodium, rubidium, ruthenium, samarium, scandium, selenium, silver, sodium, strontium, sulfur, tantalum, technetium, tellurium, terbium, thallium, thorium, thulium, tin, titanium, tungsten, uranium, vanadium, ytterbium, yttrium, zinc, zirconium, and isotopes thereof. Radioisotopes of various metals are useful in diagnostic and therapeutic applications and the particular radioisotope used will depend upon the desired end use of the metallopharmaceutical compounds. For example, gamma-emitting radionuclide metal ions such as indium-III, $^{67}$gallium and $^{99m}$technetium or beta-emitting isotopes, such as $^{186}$rhenium, $^{188}$rhenium, $^{189}$rhenium, $^{105}$rhodium, $^{153}$samarium, $^{90}$yttrium and $^{67}$copper can be used. In one embodiment, the metal is selected from the group consisting of $^{124}$Antimony, $^{125}$Antimony, $^{74}$Arsenic, $^{103}$Barium, $^{140}$Barium, $^{7}$Beryllium, $^{206}$Bismuth, $^{207}$Bismuth, $^{109}$Cadmium, $^{15m}$Cadmium, $^{45}$Calcium, $^{139}$Cerium, $^{141}$Cerium, $^{144}$Cerium, $^{137}$Cesium, $^{51}$Chromium, $^{55}$Cobalt, $^{56}$Cobalt, $^{57}$Cobalt, $^{58}$Cobalt, $^{60}$Cobalt, $^{64}$Cobalt, $^{67}$Copper, $^{169}$Erbium, $^{152}$Europium, $^{64}$Gallium, $^{68}$Gallium, $^{153}$Gadolinium, $^{157}$Gadolinium, $^{195}$Gold, $^{199}$Gold, $^{175}$Hafnium, $^{175\text{-}181}$Hafnium, $^{166}$Holmium, $^{110}$Indium, $^{111}$Indium, $^{192}$Iridium, $^{55}$Iron, $^{59}$Iron, $^{85}$Krypton, $^{210}$Lead, $^{54}$Manganese, $^{197}$Mercury, $^{203}$Mercury, $^{99}$Molybdenum, $^{147}$Neodymium, $^{237}$Neptunium, $^{63}$Nickel, $^{95}$Niobium, $^{185+191}$Osmium, $^{103}$Palladium, $^{195m}$Platinum, $^{143}$Praseodymium, $^{147}$Promethium, $^{233}$Protactinium, $^{226}$Radium, $^{186}$Rhenium, $^{188}$Rhenium, $^{86}$Rubidium, $^{103}$Ruthenium, $^{106}$Ruthenium, $^{44}$Scandium, $^{46}$Scandium, $^{75}$Selenium, $^{110m}$Silver, $^{111}$Silver, $^{22}$Sodium, $^{85}$Strontium, $^{89}$Strontium, $^{90}$Strontium, $^{35}$Sulfur, $^{182}$Tantalum, $^{99m}$Technetium, $^{125}$Tellurium, $^{132}$Tellurium, $^{204}$Thallium, $^{228}$Thorium, $^{232}$Thorium, $^{170}$Thallium, $^{113}$Tin, $^{114}$Tin, $^{117m}$Tin, $^{44}$Titanium, $^{185}$Tungsten, $^{48}$Vanadium, $^{49}$Vanadium, $^{169}$Ytterbium, $^{86}$Yttrium, $^{88}$Yttrium, $^{90}$Yttrium, $^{91}$Yttrium, $^{65}$Zinc, and $^{95}$Zirconium. In another embodiment, the metal is selected from the group consisting of Lutetium, $^{177}$Lutetium, Yttrium, $^{86}$Yttrium, $^{90}$Yttrium, Indium, $^{111}$Indium, $^{113m}$Indium, Technetium, $^{98}$Technetium, $^{99m}$Technetium, Rhenium, $^{186}$Rhenium, $^{188}$Rhenium, Gallium, $^{67}$Gallium, $^{68}$Gallium, Copper, $^{62}$Copper, $^{64}$Copper, $^{67}$Copper, Gadolinium, $^{153}$Gadolinium, Dysprosium, $^{165}$Dysprosium, $^{166}$Dysprosium, Holmium, $^{166}$Holmium, Europium, $^{169}$Europium, Samarium, $^{153}$Samarium, Palladium, $^{103}$Palladium, Promethium, $^{149}$Promethium, Thulium, $^{170}$Thulium, Bismuth, $^{212}$Bismuth, Arsenic and $^{211}$Arsenic. In another embodiment, the metal is selected from the group consisting of $^{177}$Lutetium, $^{86}$Yttrium, $^{90}$Yttrium, $^{111}$Indium, $^{113m}$Indium, $^{98}$Technetium, $^{99m}$Technetium, $^{186}$Rhenium and $^{188}$Rhenium.

Any metal coordinating moiety that can be linked to a hexose, that does not significantly interfere with cellular uptake and excretion, that has sufficient metal binding affinity and selectivity to form a stable complex with the metal, that will not quantitatively release the metal in the body, and that meets acceptable toxicological criteria is suitable for the metallopharmaceutical compounds of the present invention. Metal coordinating moieties that are linked by a ketone to an amine linker, thereby forming an amide (—N—C(O)—), are excluded from the scope of the present invention. Suitable metal coordinating moieties preferably possess properties such as, for example, size, conformation, steric attributes and charge that do not interfere with transportation of the compounds into and out of cells, or excretion from the body. Moreover, the metal coordinating moieties should possess acceptable in vivo stability such as the ability to maintain metal affinity and not substantially degrade upon exposure to metabolic processes such as enzymolysis or under physiological conditions of, for example, temperature, pH and conductivity. The choice of metal coordinating moiety is further influenced by a variety of considerations such as the identity of the metal and its oxidation state, the ease of synthesis of the metallopharmaceutical, the chemical and physical properties of the ligands, the rate of formation, the yield, and the number of isomeric forms of the resulting metallopharmaceuticals, the ability to administer the metallopharmaceutical compound to a patient without adverse physiological consequences to the patient, and the compatibility of the metal coordinating moiety in finished product forms such as a solution or lyophilized formulation.

Metal coordinating moieties having at least two degrees of dentation, such as bidentate or polydentate ligands, bidentate or polydentate ligands in combination with monodentate ligands or a combination of monodentate ligands are preferred. The ligands generally comprise donor atoms such as oxygen, nitrogen, sulfur, phosphorus, and derivatives and combinations thereof. Examples include, but are not limited to, dioxygen, aminocarboxylates, imines, nitriles, unsaturated or aromatic nitrogen-containing heterocycles, phosphines and thiocarbonyls. In one embodiment, the ligands may be substituted with, for example, alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: oxo, hydroxyl, carboxyl, carboxamide, nitro, ether, ketone, amino, ammonium, sulfonate, sulfonamide, terpyridyl, caboxymethylamino, phosphonate, and phosphonamide. The functional groups may be chosen to alter the lipophilicity and water solubility of the ligands which may affect the biological properties of the metallopharmaceuticals, such as altering the distribution into non-target tissues, cells or fluids, and the mechanism and rate of elimination from the body.

In one embodiment, the metal coordinating moiety is selected from the group consisting of cyclic metal coordinating moieties of formula (4):

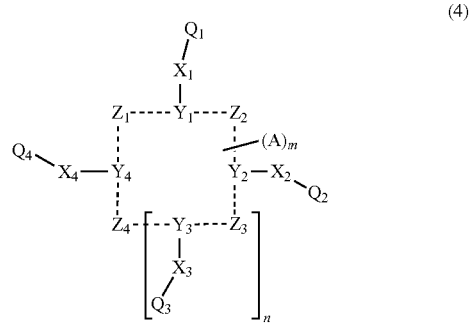

(4)

wherein
n is 0, 1 or 2;
m is 0-20 and each A is independently selected from halogen, hydroxyl, $C_{1\text{-}20}$ alkyl or aryl optionally substituted by one or more aryl, $C_{1-20}$ alkyl, carbaldehyde (—C(O)H), keto (—C(O)R), carboxyl (—$CO_2H$), cyano (—CN), halo, nitro (—$NO_2$), amido (—C(O)NHR), sulfato (—$OSO_3H$), sulfito (—$SO_3H$), phosphato (—$PO_3H_2$), phosphito (—$PO_3H_2$), hydroxyl (—OH), oxy, ether, mercapto (—SH) or thio (—SR), where R is selected from hydrogen and substituted or unsubstituted hydrocarbyl;

$Y_1$, $Y_2$, $Y_3$ and $Y_4$ are independently selected from methylene, nitrogen, sulfur and phosphorus;

$Z_1$, $Z_2$, $Z_3$ and $Z_4$ are shown with a dashed bond indicating that each are optionally, and independently present in the metal coordinating moiety compound and, when present, are independently selected from substituted or unsubstituted alkylene, alkenylene, alkynylene, heteroalkylene, heteroalkenylene and heteroalkynylene having from 1 to 8 carbon atoms. When $Z_1$, $Z_2$, $Z_3$ and/or $Z_4$ is alkyl or substituted alkyl, or alkenyl or substituted alkenyl, heteroatoms selected from oxygen, sulfur, nitrogen and phosphorus can be present. When one or more of $Z_1$, $Z_2$, $Z_3$ and/or $Z_4$ are not present, the associated Y groups are attached. For instance, if $Z_1$ is not present, a $Y_1$—$Y_4$ bond is formed;

$X_1$, $X_2$, $X_3$ and $X_4$ are independently selected from a bond, hydrocarbyl, substituted hydrocarbyl, nitrogen, phosphorus, oxygen or sulfur where the substituents are selected from the group consisting of substituted or unsubstituted aryl, $C_{1-20}$ alkyl, carbaldehyde, keto, carboxyl, cyano, halo, nitro, amido, sulfato, sulfito, phosphato, phosphito, hydroxyl, oxy, ether, mercapto and thio; and $Q_1$, $Q_2$, $Q_3$ and $Q_4$ are independently selected from the group consisting of hydrogen, hydroxyl, halogen, cyano, nitro, amido, amino, sulfito, phosphito, sulfato, phosphato, ether, hydrocarbyl and substituted hydrocarbyl. For example, $Q_1$, $Q_2$, $Q_3$ and $Q_4$ can be independently selected from the group consisting of fluoro, chloro, bromo, iodo, carboxyl, cyano, nitro, amido, hydroxyl, amino, mercapto, thio, sulfito, phosphito, sulfato, phosphato, ether, aryl, or $C_{1-20}$ alkyl, $C_{1-20}$ substituted alkyl, aryl and substituted aryl. In one embodiment, $Q_1$, $Q_2$, $Q_3$ and $Q_4$ are independently selected from the group consisting of hydrogen, hydroxyl, carboxyl, bromo, iodo, 1-hydroxyphenyl, 1-bromoacetamidephenyl, 1-formylphenyl, 1-thiolphenyl, 1,3-dihydroxyphenyl, 3,5-dihyroxypyridyl, 2,4-dihydroxypyridyl, 4,6-dihydroxypyrimidyl, 1,3-dithiolphenyl, 3,5-dithiolpyridyl, 2,4-dithiolpyridyl, 4,6-dithiolpyrimidyl, 1-hydroxy-3-thiolphenyl, 3-hydroxy-5-thiolpyridyl, 2-hydroxy-4-thiolpyridyl, 4-hydroxy-6-thiolpyrimidyl, 1-thiol-3-hydroxyphenyl, 3-thiol-5-hydroxypyridyl, 2-thiol-4-hydroxypyridyl, 4-thiol-6-hydroxypyrimidyl, methylthio, phosphanate, and sulfonate.

$Q_1$, $Q_2$, $Q_3$ and $Q_4$ are optionally substituted at each substitutable carbon atom by D, wherein each D is independently selected from the group consisting of the linker connecting the metal coordinating moiety to the hexose carrier, fluoro, chloro, bromo, iodo, carboxyl, cyano, nitro, amido, mercapto, thio, hydroxyl, amino, sulfito, phosphito, sulfato, phosphato, ether, aryl, or $C_{1-8}$ alkyl optionally substituted with one or more of $C_{1-20}$ alkyl, carboxyl, cyano, nitro, amido, hydroxyl, amino, sulfito, phosphito, sulfato, and phosphate. More typically, each D is bromo, iodo, carboxyl, or hydroxyl. In another embodiment, the metal coordinating moiety is connected to the hexose carrier, either directly or indirectly, via a D group.

Representative examples of formula (4) compounds include, but are not limited to, the following:

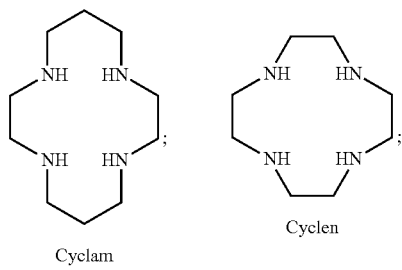

Cyclam

Cyclen

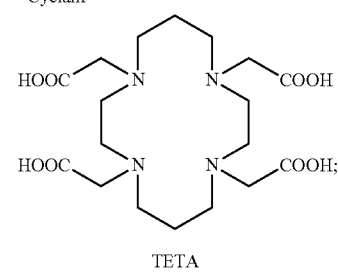

TETA

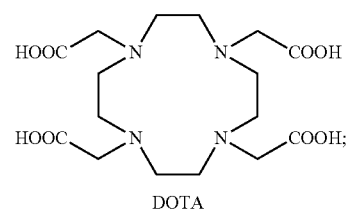

DOTA

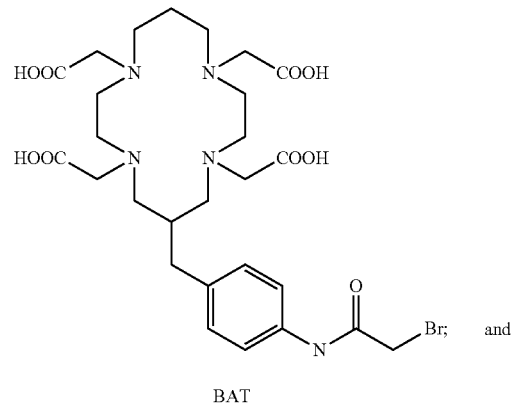

BAT and

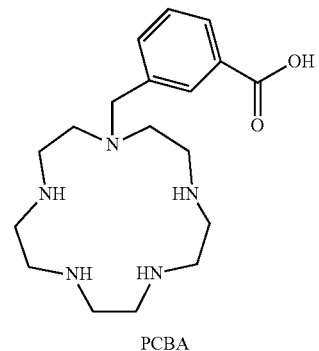

PCBA

In another embodiment, the metal coordinating moiety is a tertiary amine of formula (5)

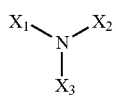

(5)

wherein $X_1$, $X_2$ and $X_3$ are independently ligands selected from hydrocarbyls and substituted hydrocarbyls where at least two hydrocarbyls are preferably substituted. The ligands may be independently substituted with, for example, the linker, halogen, oxo, hydroxyl, carboxyl, nitro, amino, amido, mercapto, thio or phospho. The substituted ligands may further comprise heteroatoms such as oxygen, nitrogen, phosphorus or sulfur. In one embodiment, $X_1$ and $X_2$ are ligands and $X_3$ is a moiety bound to the linking group.

Representative examples of formula (5) compounds include, but are not limited to, the following:

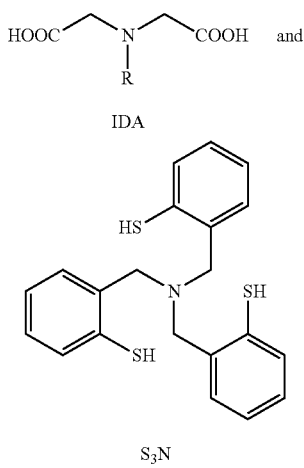

wherein R is hydrocarbyl or substituted hydrocarbyl.

In another embodiment, the metal coordinating moiety the metal coordinating moiety is a poly amine of formula (6)

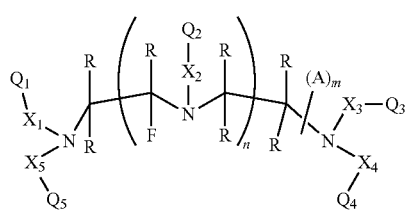

(6)

wherein n is 0, 1 or 2;

m is 0-12 wherein when m is greater than 0, each A is $C_{1-20}$ alkyl or aryl optionally substituted by one or more aryl, $C_{1-20}$ alkyl, carbaldehyde, keto, carboxyl, cyano, halo, nitro, amido, sulfato, sulfito, phosphato, phosphito, hydroxyl, oxy, ether, mercapto or thio;

$X_1$, $X_2$, $X_3$, $X_4$ and $X_5$ are independently a bond or an optionally substituted $C_{1-20}$ hydrocarbylene where the substituents are selected from the group consisting of aryl, $C_{1-20}$ alkyl, carbaldehyde, keto, carboxyl, cyano, halo, nitro, amido, sulfato, sulfito, phosphato, phosphito, hydroxyl, oxy, ether, mercapto and thio;

Each R is independently hydrogen or an optionally substituted $C_{1-20}$ hydrocarbyl where the substituents are selected from the group consisting of aryl, $C_{1-20}$ alkyl, carbaldehyde, keto, carboxyl, cyano, halo, nitro, amido, sulfato, sulfito, phosphato, phosphito, hydroxyl, oxy, ether, mercapto and thio; and $Q_1$, $Q_2$, $Q_3$, $Q_4$, and $Q_5$ are independently selected from the group consisting of hydrogen, hydroxyl, carboxyl, halogen, cyano, nitro, amido, amino, sulfito, phosphito, sulfato, phosphato, mercapto, thio, ether, hydrocarbyl and substituted hydrocarbyl. For example, $Q_1$, $Q_2$, $Q_3$, $Q_4$ and $Q_5$ can be independently selected from the group consisting of fluoro, chloro, bromo, iodo, carboxyl, cyano, nitro, amido, hydroxyl, amino, mercapto, thio, sulfito, phosphito, sulfato, phosphato, ether, aryl, or $C_{1-20}$ alkyl, $C_{1-20}$ substituted alkyl, aryl and substituted aryl. In one embodiment, $Q_1$, $Q_2$, $Q_3$, $Q_4$ and $Q_5$ are independently selected from the group consisting of hydrogen, hydroxyl, carboxyl, bromo, iodo, 1-hydroxyphenyl, 1-bromoacetamidephenyl, 1-formylphenyl, 1-thiolphenyl, 1,3-dihydroxyphenyl, 3,5-dihyroxypyridyl, 2,4-dihydroxypyridyl, 4,6-dihydroxypyrimidyl, 1,3-dithiolphenyl, 3,5-dithiolpyridyl, 2,4-dithiolpyridyl, 4,6-dithiolpyrimidyl, 1-hydroxy-3-thiolphenyl, 3-hydroxy-5-thiolpyridyl, 2-hydroxy-4-thiolpyridyl, 4-hydroxy-6-thiolpyrimidyl, 1-thiol-3-hydroxyphenyl, 3-thiol-5-hydroxypyridyl, 2-thiol-4-hydroxypyridyl, 4-thiol-6-hydroxypyrimidyl, methylthio, phosphanate, and sulfonate.

$Q_1$, $Q_2$, $Q_3$, $Q_4$ and $Q_5$ are optionally substituted at each substitutable carbon atom by D wherein each D is independently selected from the group consisting of the linker connecting the metal coordinating moiety to the hexose carrier, fluoro, chloro, bromo, iodo, carboxyl, cyano, nitro, amido, hydroxyl, amino, mercapto, thio, sulfito, phosphito, sulfato, phosphato, ether, aryl, or $C_{1-8}$ alkyl optionally substituted with one or more of $C_{1-20}$ alkyl, carboxyl, cyano, nitro, amido, hydroxyl, amino, sulfito, phosphito, sulfato, and phosphate. More typically, each D is bromo, iodo, carboxyl, or hydroxyl. In another embodiment, the metal coordinating moiety is connected to the hexose carrier, either directly or indirectly, via a D group.

Typically, for metal coordinating moieties of Formula (6), $X_1$, $X_2$, $X_3$, $X_4$ and $X_5$ are independently $C_{1-8}$ alkylene are optionally substituted by $C_{1-6}$ alkyl, halo, or hydroxyl.

In another embodiment of metal coordinating moieties of Formula (6), one of $Q_1$, $Q_2$, $Q_3$, $Q_4$ and $Q_5$ is substituted by D, while the other four of $Q_1$, $Q_2$, $Q_3$, $Q_4$ and $Q_5$ are not substituted by D. Typically, in this embodiment, D is the linker connecting the metal coordinating moiety to one or more hexose carriers.

In another embodiment, $X_1$-$Q_1$ and $X_5$-$Q_5$ and the nitrogen to which they are attached and/or $X_3$-$Q_3$ and $X_4$-$Q_4$ and the nitrogen to which they are attached independently form a 4 to 6 membered substituted or unsubstituted ring comprising carbon and nitrogen atoms, and optionally further substituted within the ring with one or more heteroatoms selected from sulfur, oxygen and phosphorus.

When the metal coordinating moiety corresponds to Formula (6) and m is greater than 0, it is generally preferred that each A be a substituent that positively impacts stability and biodistribution. When present, each A may independently be substituted with one or more aryl, $C_{1-20}$ alkyl, carbaldehyde, keto, carboxyl, cyano, halo, nitro, amido, sulfato, sulfito, phosphato, phosphito, hydroxyl, oxy, ether, $C_4$-$C_{20}$ carbohydrate, mercapto, or thio substituents. In addition, when A is aryl or alkyl, each of these, in turn, may be optionally substituted with an aryl or $C_{1-20}$ alkyl moiety optionally substituted with one or more aryl, carbaldehyde, keto, carboxyl, cyano, halo, nitro, amido, sulfato, sulfito, phosphato, phosphito, hydroxyl, oxy, mercapto and thio.

Further, for the metal coordinating moieties of Formula (6), the A substituent, if present, is bonded to any of the backbone carbon atoms. Still further, each backbone carbon atom may be substituted by one or two A substituents so that the number of possible A substituents varies with the number of carbon atoms. In one embodiment of metal coordinating moieties of Formula (6) having at least one A substituent, each A is independently aryl or $C_{1-8}$ alkyl optionally substituted with one or more aryl, keto, carboxyl, cyano, nitro, $C_{1-20}$ alkyl, amido, sulfato, sulfito, phosphato, phosphito, oxy, mercapto and thio. For example, each A may be aryl or $C_{1-6}$ alkyl optionally substituted with one or more aryl, keto, amido and oxy. By way of further example, each A may be methyl.

In general, as the value of n increases, the length of the chain of atoms increases. In that manner, the length of the backbone may be controlled to match the size and coordination capacity of the metal to be coordinated.

Representative examples of formula (6) compounds include, but are not limited to, the following:

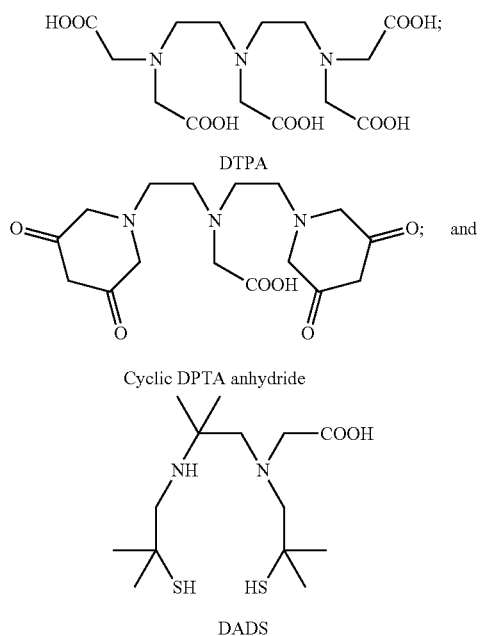

DTPA

Cyclic DPTA anhydride

DADS

In one embodiment, metal coordinating moieties of formulae (4) to (6) are selected from the group consisting of cyclic and acyclic monoamine carboxylates; cyclic and acyclic polyaminocarboxylates; and cyclic and acyclic aminethiols, diaminedithiols, monoamine-monoamidedithiols, triamidemonothiols, monoamine-diamide-monothiols, diaminedioximes and hydrazines.

In another embodiment, metal coordinating moieties of formulae (4) to (6) are selected from the group consisting of: diethylenetriaminepentaacetic anhydride (DTPA) and DTPA derivatives such as 2-benzyl-cyclohexyldiethylenetriaminepentaacetic acid, 2-benzyl-6-methyl-DTPA, N-[2-amino-3-(rho-nitrophenyl)propyl]-trans-cyclohexane-1,2-diamine-N,N',N'''-pentaacetic acid (nitro-CHX-A-DTPA) and 2-methyl-6-(rho-nitrobenzyl)-1,4,7-triazaheptane-N,N,N',N'',N''-pentaacetic acid (nitro-1B4M-DTPA or nitro-MX-DTPA); diethylenetriaminetetraacetic acid (DTTA) and DTTA derivatives; 6,6''-bis[[N,N,N'',N''-tetra(carboxymethyl)amino]methyl]-4'-(3-amino-4-methoxyphenyl)-2,2':6', 2''-terpyridine (TMT-amine) and TMT-amine derivatives; 1,4,7,10-tetraazacyclododecane-N,N',N'',N'''-tetraacetic acid (DOTA) and DOTA derivatives such as 2-benzyl-DOTA, DOTA-N-hydroxysuccinimide, 2-(rho-nitrobenzyl)-1,4,7, 10-tetraazacyclododecane-N,N',N'',N'''-tetraacetic acid (nitro-DOTA), and alpha-(2-(rho-nitrophenyl)ethyl)-1,4,7,10,-tetraazacyclododecane-1-acetic-4,7,10-tris(methylacetic) acid (nitro-PADOTA); 1,4,7-triazacyclononane-N,N',N''-triacetic acid and derivatives thereof; 2-(rho-nitrobenzyl)-1,4, 7,10-tetraazacyclotridecane-N,N',N'',N'''-tetraacetic acid (nitro-TRITA); ethylenediaminetetra (methylene phosphonate (EDTMP) and EDTMP derivatives; N-hydroxyethylethylene-diaminetriacetic acid (HEDTA) and HEDTA derivatives; 1,1-hydroxyethylidine diphosphonate (HEDP) and HEDP derivatives; 1,4,8,11-tetraazacyclo-tetradecane-1,4,8,11-tetracetic acid (TETA) and TETA derivatives such as SCN-TETA and 6-bromoacetamido-benzyl-1,4,8,11-tetraazacyclotetadecane-N,N',N'',N'''-tetraacetic acid; tetra-tertbutyl-calix[4]arene-crown-6-dicarboxylic acid (TBBCDA) and TBBCDA derivatives; 5,11,17,23-tetra-t-butyl-25,26,27,28-tetrakis(carboxymethoxy)-calix[4]arene (TBTC) and TBTC derivatives; 5,11,17,23,29,35-hexa-t-butyl-37,38,39,40,41, 42 hexakis(carboxymethoxy)-cal ix[6]arene (HBHC) and HBHC derivatives; hexamethylpropyleneamine oxime (HMPAO) and HMPAO derivatives; alpha-(2-phenethyl)1,4,7,10-tetraazacyclododecane-1-acetic-4,7,10-tris(methylacetic) acid; 6,6''-bis[N,N,N'',N''-tetra(carboxymethyl)aminoethyl)-4'-(3-amino-4-methoxyphenyl)-2,2':6',2'-terpyridine and derivatives thereof; ethylenediaminetetraacetic acid (EDTA) and EDTA derivatives; deoxymugenic acid (DMA) and DMA derivatives; mugenic acid (MA) and MA derivatives; nicotianamine (NA) and NA derivatives; carbonyliminodiacetic acid and derivatives thereof; methyleneiminoacetic acid and derivatives thereof; methyleneiminodiacetic acid and derivatives thereof; ethylenethioethylene-iminoacetic acid and derivatives thereof; ethylenethioethylene-iminodiacetic acid and derivatives thereof; iminodiacetic acid (IDA) and IDA derivatives; 2,3-diaminopropionic acid and derivatives thereof; hexakis-2-methoxyisobutyl isonitrile (MIBI) and MIBI derivatives; nitrilotriacetic acid and derivatives thereof; N,N'-ethylenediamine diacetic acid and derivatives thereof; N,N,N'-ethylenediamine triacetic acid and derivatives thereof; hydroxyethylethylene-diamine triacetic acid and derivatives thereof; N,N,N'-trimethyl-N'-(2-hydroxy3-methyl-5-iodobenzyl)-1,3-propane diamine (HIPDM) and HIPDM derivatives; N-(2-(1H pyrolylmethyl)N'-(4-pentene-3-one-2))ethane-1,2-diamine (MRP-20) and MRP-20 derivatives; N,N'-ethylenediamine bis-hydroxyphenylglycine and derivatives thereof; desferrioxamine (DFOA), and DFOA derivatives; 4,5-dihydroxy-1,3-benzene disulfonate and derivatives thereof; N-alkyl substituted 3,4-hydroxypyridinones and derivatives thereof; dimercaptosuccinic acid (DMSA), and DMSA derivatives; dimercaptopropionic sulfonate (DMPS) and derivative thereof; tris(2-mercaptobenzyl)amine ($S_3N$) and $S_3N$ derivatives; bis-amino bis-thiol (BAT) and BAT derivatives; mercapto-acetyl diglycine and derivatives thereof; mercapto-acetyl triglycine (MAG3) and derivatives thereof; monoamide-monoamine bisthiol (MAMA or $N_2S_2$) and MAMA derivatives; $N_2S_2$ diaminodithiolate (DADT) and DADT derivatives; $N_2S_2$ diamidedithiol (DADS) and DADS derivatives; bis(N-ethyl, N-ethoxy dithiocarbamate) (NOET) and NOET derivatives; bis(diethyldithio-carbamato)nitride and derivatives thereof; p-carboxyethylphenylglyoxal di(N-methylthiosemicarbazone) (CE-DTS) and CE-DTS derivatives; propylene amine oxime (PnAO) and PnAO derivatives; bis(thiosemicarbazone)

(DTS) and DTS derivatives; D-penicillamine (DPA) and DPA derivatives; British Anti-Lewisite (2,3-dimercaptopropanol (BAL)) and BAL derivatives; 1,4,7,10-tetraazacyclododecane (cyclen) and cyclen derivatives such as 1,7-bis(carboxymethyl)-1,4,7,10-tetraazacyclododecane (DO2A) and 1,4,7,10-tetraazacyclododecane-5,7-dione (and also the cis-, gem- and trans-forms); 1,4,8,11-tetraazacyclotetradecane (cyclam) and cyclam derivatives such as methylcyclam, 1,8-bis(pyridylmethyl)cyclam, 1,11-bis(pyridylmethyl)cyclam, 4-[1,4,8,11-tetraazacyclotetradec-1-yl]-methylbenzoic acid (CPTA), 1,4,8,11-tetraazacyclotetradecane-3,9,-dione, and dioxycyclam (gem-, cis- and trans-forms); 1,4,7,10-tetrazazcyclotridecane-11,13-dione, 1,4,7,10-tetrazazcyclotridecane-2,9-dione and 1,4,7,10-tetrazazcyclotridecane-3,8-dione; 1,4,7,10,13-pentaazacyclopentadecane (PCBA) and PCBA derivatives; pyruvaldehyde bis(N(4)-methyl)thiosemicarbazone (PTSM) and PTSM derivatives; hydrazinonicotinamide (HYNIC) and HYNIC derivatives; N,N'-1,2-ethanediylbis-L-cysteine diethylester (ECD) and ECD derivatives; N-hydroxysuccinimidyl hydrazinonicotinate and derivatives thereof including the bis(hydroxyamide) derivative; and homologues, analogs and isomers thereof, or combinations thereof.

For any of the above embodiments, the metal coordinating moiety is complexed with a metal, M, thereby forming a metal complex. For example, in one embodiment where the metal coordinating moiety is a heterocyclic ring and complexed with a metal, M, the complex has the following Formula (7):

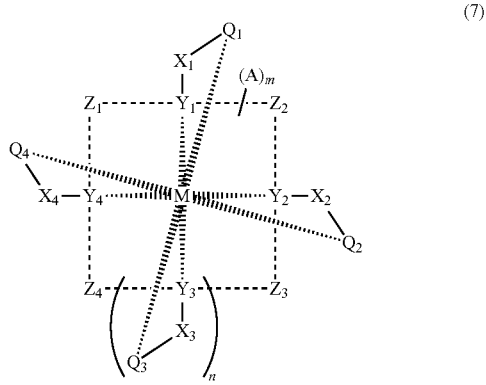

(7)

wherein A, $Q_1$, $Q_2$, $Q_3$, $Q_4$, $Y_1$, $Y_2$, $Y_3$, $Y_4$, $X_1$, $X_2$, $X_3$, $X_4$, $Z_1$, $Z_2$, $Z_3$, $Z_4$, m and n are as defined above for formula (4).

Alternatively, in one embodiment where the metal coordinating moiety comprises a chain of atoms and is complexed with a metal, M, the complex has the following Formula (8):

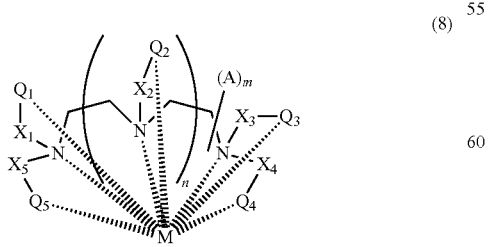

(8)

wherein A, $Q_1$, $Q_2$, $Q_3$, $Q_4$, $X_1$, $X_2$, $X_3$, $X_4$, m and n are as defined above for formula (6).

In one embodiment where the metal coordinating moiety comprises a chain of atoms and it is complexed with a metal, M, the complex has the following Formula (9):

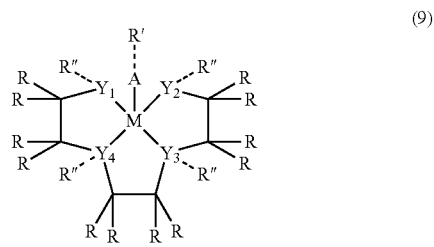

(9)

wherein: M represents a metal; the dashed bonds indicate that the R' and R" substituents are optionally present; A is oxygen, nitrogen, carbon or phosphorus, but when A is oxygen R' is not present; the bond between A and M is shown as a single bond, but it may be a double bond; $Y_1$, $Y_2$, $Y_3$ and $Y_4$ are independently selected from sulfur, oxygen, carbon and phosphorus; R, R' and R" are independently selected from hydrogen, halogen, $C_{1-20}$hydrocarbyl, $C_{1-20}$ substituted hydrocarbyl, carboxyl, cyano, nitro, amido, hydroxyl, amino, sulfato, sulfito, phosphato, and phosphito; and when R" is present and $Y_3$ and/or $Y_4$ are nitrogen, the $Y_3$ and/or $Y_4$ nitrogen is in the quaternary form. The carbon atoms in the ethylene groups linking $Y_1$ to $Y_4$, $Y_2$ to $Y_3$ or $Y_3$ to $Y_4$ can optionally be replaced with a heteroatom selected from oxygen, nitrogen, sulfur and phosphorus. Any one of R, R' or R" can be bound to the group linking the metal coordinating moiety to the hexose carrier. In one embodiment A is oxygen and the bond between A and M is a double bond. Representative examples include, but are not limited to, DADT, MAMA, $N_2S_2$, HYNIC and BATO, the chemical name of which for each is given above.

Yet another example of a chelation complex formed from a chain of atoms and a metal, M, is shown by formula (10) which is directed to metal coordinating moieties having a combination of monodentate and polydentate ligands such as tridentate or quatradentate, known in the art as "3+1" and "4+1", respectively. Formula (10) depicts a "3+1" conformation:

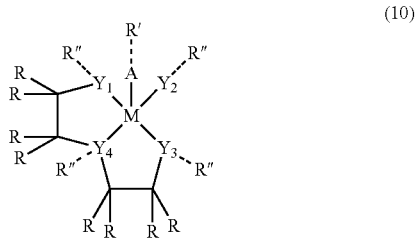

(10)

wherein M, A, Y, R, R' and R" are as described above for formula (9) and —$Y_2$—R" is a monodentate ligand. Linkage to the hexose carrier can occur at any one of R, R' or R". In this embodiment, the -A substituent is non-chelating, such as oxo, i.e., where the bond between A and M is a double bond instead of the depicted single bond, A is oxygen and R' is not present. A "4+1" chelation complex would be formed from formula (10) when the -A substituent is a monodentate ligand.

An example of a metallopharmaceutical compound of the present invention (the chelated metal is not shown) is directed to a DOTA metal coordinating moiety (i.e., a cyclic metal coordinating moiety of formula (4)) linked to a glucose carrier at the C-6 position by a secondary amine linker as represented by formula (11):

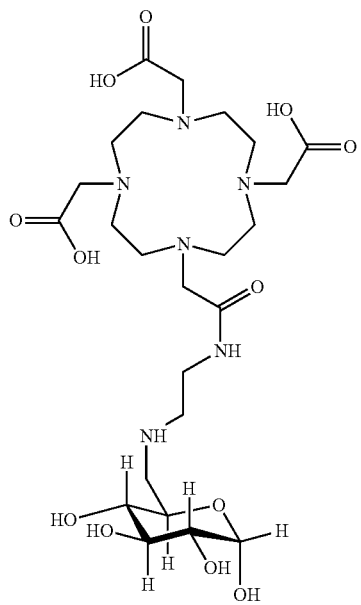

(11)

Another example of a metallopharmaceutical compound of the present invention (the chelated metal is not shown) is directed to an IDA metal coordinating moiety (i.e., a tertiary amine metal coordinating moiety of formula (5)) linked to a glucose carrier at the C-6 position by a secondary amine linker as represented by formula (12):

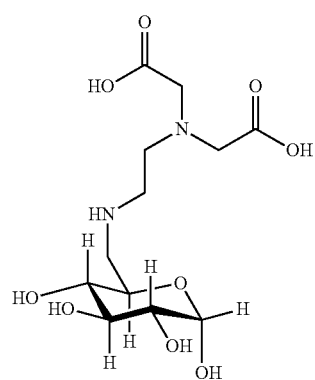

(12)

Another example of a metallopharmaceutical compound of the present invention (the chelated metal is not shown) is directed to a DTPA metal coordinating moiety (i.e., a tertiary amine metal coordinating moiety of formula (6)) linked to a glucose carrier at the C-6 position by a secondary amine linker as represented by formula (13):

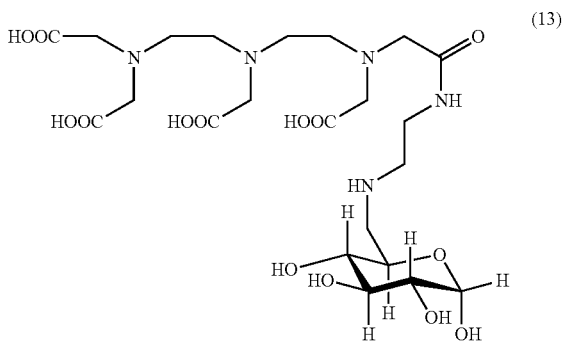

(13)

The compounds of the present invention may be synthesized in a variety of ways.

In one scheme, a conjugate of the metal coordinating moiety and linker can be formed that is subsequently coupled with a hexose molecule. For example, the tris(tert-butyl)ester analogs of the metal coordinating moieties DOTA (DO3A-tris(tert-butyl)ester) or TETA (TE3A-tris(tert-butyl)ester) can be alkylated with an amine such as benzyl 2-(2-bromoacetamido)ethylcarbamate in acetonitrile and sodium carbonate followed by hydrogenolysis in the presence of a catalyst, such as palladium on carbon, to yield the free amine metal coordinating moiety-linker conjugate. The free amine can then be alkylated by a tosylated, protected, hexose such as 6-tosyl-2,3,4,5-tetra-O-acetyl glucose and deprotected, such as by saponification with a base (e.g., sodium hydroxide) and aqueous methanol, followed by treatment with trifluoroacetic acid, to form the glucose conjugate compound.

In another scheme, a conjugate of the hexose and linker can be formed that is subsequently coupled to the metal coordinating moiety. For example, an amine such as mono(carbobenoxyl)ethylenediamine may be mono-alkylated with a protected hexose such as 6-tosyl-2,3,4,5-tetra-O-acetyl glucose and an organic base such as triethylamine. The primary amine hexose-linker conjugate may then be prepared by hydrogenolysis in the presence of a catalyst, such as palladium on carbon. The hexose-linker can then be acetylated with an anhydride such as DTPA-bis(anhydride) to yield a protected mono-acylate intermediate that can be purified by suitable means, such as by reverse phase chromatography. A glucose conjugate compound of the present invention may be prepared from the intermediate by saponification with a base (e.g., sodium hydroxide) and aqueous methanol.

In yet another scheme, a compound that serves both the linker and metal coordinating functions is coupled to the hexose. For example, an amine such as tert-butyl 2,2'-(2-aminoethylazanediyl)diacetate can be treated with a protected hexose such as 6-tosyl-2,3,4,5-tetra-O-acetyl glucose and an organic base such as triethylamine to generate an intermediate that can be purified by suitable means, such as by reverse phase chromatography. A glucose conjugate compound of the present invention may be prepared from the intermediate by saponification with a base (e.g., sodium hydroxide) and aqueous methanol, followed by treatment with trifluoroacetic acid.

For administration to the body, the metallopharmaceutical compounds of the present invention are dispersed in a pharmaceutically acceptable carrier. The pharmaceutically acceptable carrier, also known in the art as an excipient, vehicle, auxiliary, adjuvant, or diluent, is typically a substance which is pharmaceutically inert, confers a suitable consistency or form to the composition, and does not diminish the therapeutic or diagnostic efficacy of the conjugate. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the metallopharmaceutical compositions of the invention can be formulated for any route of administration so long as the target tissue is available via that route. For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: the particular conjugate used, and its concentration, stability and intended bioavailability; the disease, disorder or condition being treated or diagnosed with the composition; the subject, its age, size and general condition; and the route of administration. Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamideamides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methyl pyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the invention are well known to those of ordinary skill in the art, and are identified in *The Chemotherapy Source Book* (Williams & Wilkens Publishing), *The Handbook of Pharmaceutical Excipients*, (American Pharmaceutical Association, Washington, D.C., and The Pharmaceutical Society of Great Britain, London, England, 1968), *Modern Pharmaceutics*, (G. Banker et al., eds., 3d ed.)(Marcel Dekker, Inc., New York, N.Y., 1995), *The Pharmacological Basis of Therapeutics*, (Goodman & Gilman, McGraw Hill Publishing), *Pharmaceutical Dosage Forms*, (H. Lieberman et al., eds.)(Marcel Dekker, Inc., New York, N.Y., 1980), *Remington's Pharmaceutical Sciences* (A. Gennaro, ed., 19th ed.)(Mack Publishing, Easton, Pa., 1995), *The United States Pharmacopeia 24, The National Formulary 19*, (National Publishing, Philadelphia, Pa., 2000), A. J. Spiegel et al., and Use of Nonaqueous Solvents in Parenteral Products, JOURNAL OF PHARMACEUTICAL SCIENCES, Vol. 52, No. 10, pp. 917-927 (1963).

Dosage and regimens for the administration of the metallopharmaceutical compositions of the invention can be readily determined by those with ordinary skill in diagnosing disease. It is understood that the dosage of the compositions is dependent upon the age, sex, health, and weight of the recipient, kind of concurrent treatment, if any, frequency of treatment, and the nature of the effect desired. For any mode of administration, the actual amount of conjugate delivered, as well as the dosing schedule necessary to achieve the advantageous effects described herein, will also depend, in part, on such factors as the bioavailability of the conjugate, the disorder being diagnosed, the desired diagnostic dose, and other factors that will be apparent to those of skill in the art. The dose administered to an animal, particularly a human, in the context of the present invention should be sufficient to affect the desired diagnostic response in the animal over a reasonable period of time.

Radiolabeled imaging agents provided by the present invention are provided having a suitable amount of radioactivity. In forming diagnostic radioactive complexes, it is generally preferred to form radioactive complexes in solutions containing radioactivity at concentrations of from about 0.01 millicurie (mCi) to 100 mCi per mL. Generally, the unit dose to be administered has a radioactivity of about 0.01 mCi to about 100 mCi, preferably about 1 mCi to about 30 mCi. The solution to be injected at unit dosage is from about 0.01 mL to about 10 mL. The amount of radiolabeled compound appropriate for administration is dependent upon the distribution profile of the chosen conjugate in the sense that a rapidly cleared conjugate may need to be administered in higher doses than one that clears less rapidly. In vivo distribution and localization can be tracked by standard scintigraphic techniques at an appropriate time subsequent to administration; typically between thirty minutes and 180 minutes depending upon the rate of accumulation at the target site with respect to the rate of clearance at the non-target tissue.

Typically, an In-111 diagnostic dose is 3-6 mCi while a typical Tc-99m does is 10-30 mCi. Generally, radiotherapeutic doses of radiopharmaceuticals vary to a greater extent, depending on the tumor and number of injections of cycles. For example, cumulative doses of Y-90 range from about 100-600 mCi (20-150 mCi/dose), while cumulative doses of Lu-177 range from about 200-800 mCi (50-200 mCi/dose).

For convenience, metallopharmaceutical compositions of the present invention may be provided to the user in the form of a kit containing some or all of the necessary components. The use of a kit is particularly convenient since some of the components, e.g., a radioisotope, have a limited shelf life, particularly when combined. Thus, the kit may include one or more of the following components (i) a conjugate, (ii) a metal coordinated to or for coordination by the conjugate, (iii) a carrier solution, and (iv) instructions for their combination and use. Depending on the metal, a reducing agent may be desired to prepare the metal for reaction with the conjugate. Exemplary reducing agents include Ce (III), Fe (II), Cu (I), Ti (III), Sb (III), and Sn (II). Of these, Sn (II) is particularly preferred. Often the components of the kit are in unit dosage form (e.g., each component in a separate vial).

For reasons of stability, it may be preferred that the conjugate be provided in a dry, lyophilized state. The user may then reconstitute the conjugate by adding the carrier or other solution.

Because of the short half-life of suitable radionuclides, it will frequently be most convenient to provide the kit to the user without a radionuclide. The radionuclide is then ordered separately when needed for a procedure. Alternatively, if the radionuclide is included in the kit, the kit will most likely be shipped to the user just before it is needed.

In addition to the metal coordinating moiety, biomolecule, active urea, metal and deprotecting acid, the kit of the present invention typically includes a buffer. Exemplary buffers include citrate, phosphate and borate.

The kit optionally contains other components frequently intended to improve the ease of synthesis of the radiopharmaceutical by the practicing end user, the ease of manufacturing the kit, the shelf-life of the kit, or the stability and shelf-life of the radiopharmaceutical. Such components of the present invention include lyophilization aids, e.g., mannitol, lactose, sorbitol, dextran, Ficoll, and polyvinylpyyrolidine (PVP); stabilization aids, e.g., ascorbic acid, cysteine, monothioglycerol, sodium bisulfite, sodium metabisulfite, gentisic acid, and inositol; and bacteriostats, e.g., benzyl alcohol, benzalkonium chloride, chlorbutanol, and methyl, propyl, or butyl paraben.

Typically, when the conjugate is formulated as a kit, the kit comprises multiple vials consisting of a protected metal coordinating moiety having an active urea group, a deprotecting acid, a buffer, and a solution of a radioactive metal such as, but not limited to, In-111, Y-90 or Lu-177. In practice, the user will take the vial containing the metal coordinating moiety and add a solution of a bio-directing carrier of interest bearing a reactive amino ($NH_2$) group. Once conjugation is complete, the deprotecting acid is added to affect deprotection, followed by addition of the radioactive metal. The mixture is then buffered to complete complexation of the radioactive metal by the metal coordinating moiety.

ABBREVIATIONS AND DEFINITIONS

The compounds described herein may have asymmetric centers. Compounds of the present invention containing an asymmetrically substituted atom may be isolated in optically active or racemic form. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The present invention includes all isotopes of atoms occurring in the present compounds. Isotopes include those atoms having the same atomic number but different mass numbers.

The following definitions and methods are provided to better define the present invention and to guide those of ordinary skill in the art in the practice of the present invention. Unless otherwise noted, terms are to be understood according to conventional usage by those of ordinary skill in the relevant art.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, sulfur, or a halogen atom. These substituents include halogen, heterocyclo, alkoxy, alkenoxy, alkynoxy, aryloxy, oxo, hydroxy, keto, acyl, acyloxy, nitro, amino, amido, nitro, cyano, thiol, ketals, acetals, esters, ethers, and thioethers.

The term "heteroatom" shall mean atoms other than carbon and hydrogen.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl, and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The terms "halogen" and "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "acyl," as used herein alone or as part of another group, denotes the moiety formed by removal of the hydroxy group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

The term "metallopharmaceutical" as used herein refers to a pharmaceutically acceptable compound comprising a metal, wherein the compound is useful for imaging or treatment.

EXAMPLES

The following examples are prophetic.

Example 1

Preparation of the Metallopharmaceutical Compound DOTA 6-Aminoglucose of Formula (11)

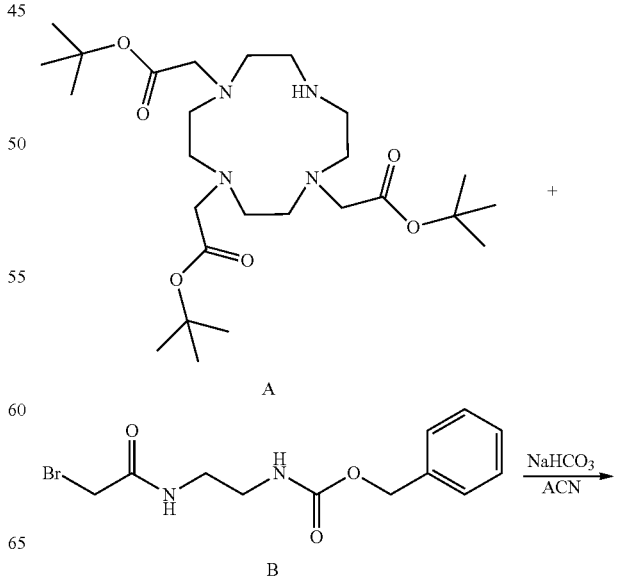

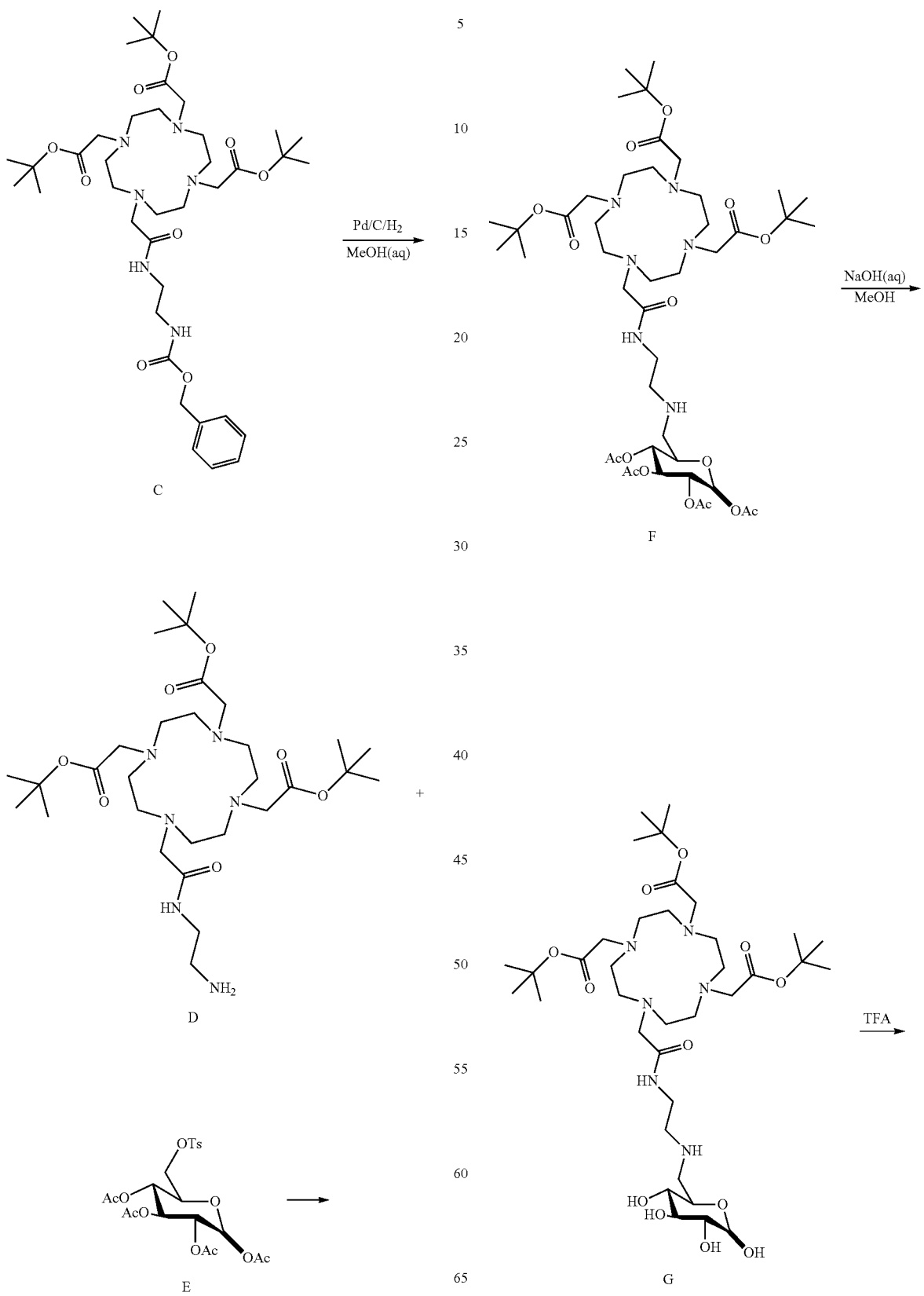

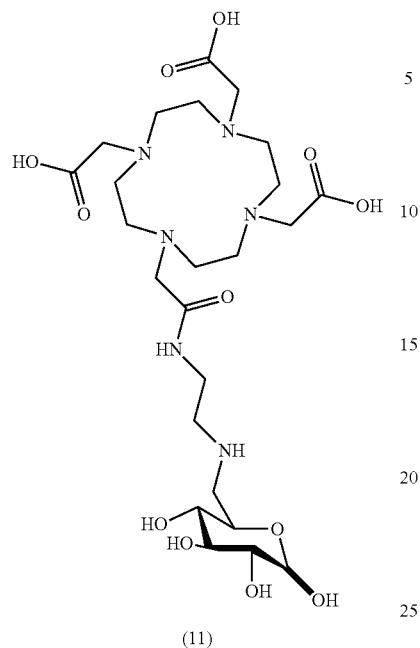

(11)

DO3A-tris(tert-butyl) ester (A) is alkylated with benzyl 2-(2-bromoacetamido)ethylcarbamate (B) in acetonitrile and sodium bicarbonate. The carbenzoxy group is removed by hydrogenolysis and the resulting free amine (D) is alkylated by 6-tosyl-2,3,4,5-tetra-O-acetyl glucose (E). The glucose conjugate, (F), may be deprotected sequentially via saponification and treatment with trifluoroacetic acid to give the free chelator (11), probably as the TFA-salt.

Example 2

Preparation of the Metallopharmaceutical Compound Iminodiacetic Acid 6-Aminoglucose of Formula (12)

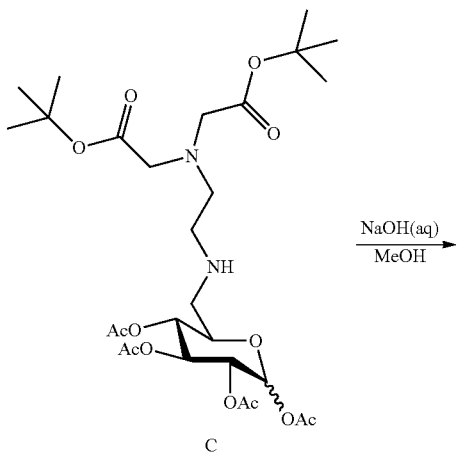

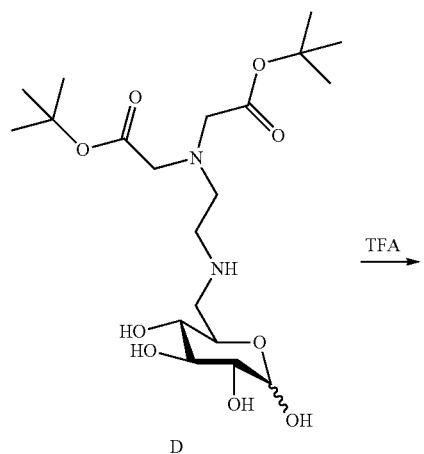

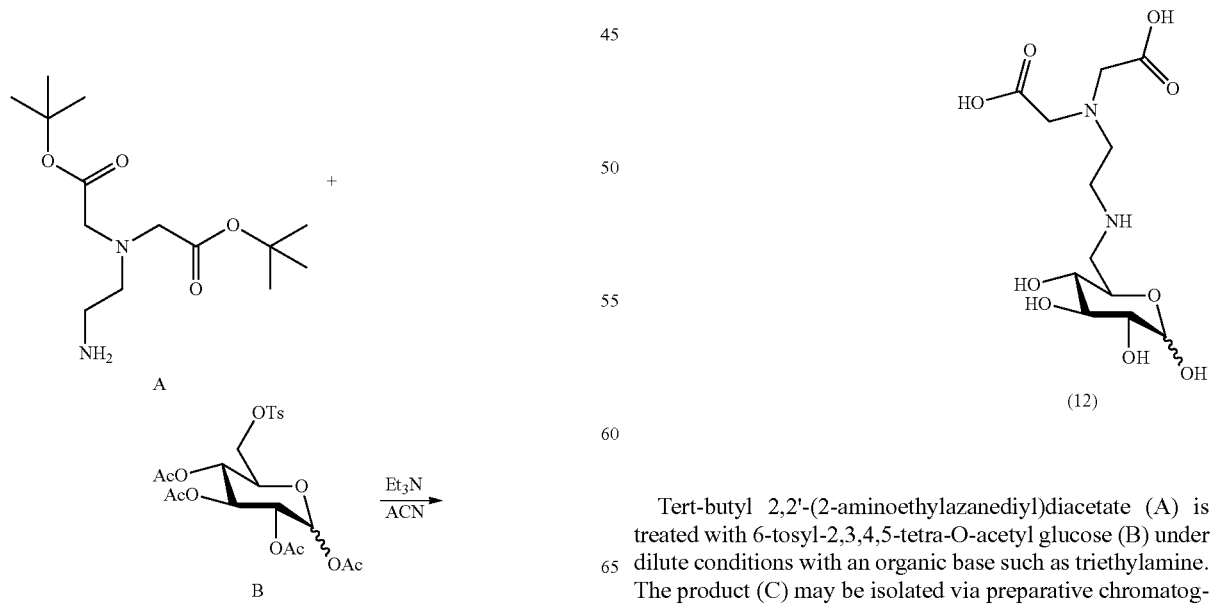

(12)

Tert-butyl 2,2'-(2-aminoethylazanediyl)diacetate (A) is treated with 6-tosyl-2,3,4,5-tetra-O-acetyl glucose (B) under dilute conditions with an organic base such as triethylamine. The product (C) may be isolated via preparative chromatography and deprotected sequentially via saponification and treatment with trifluoroacetic acid to give the free chelator (12), probably as the TFA-salt.

Example 3

Preparation of the Metallopharmaceutical Compound DTPA-6-Aminoglucose of Formula (13)

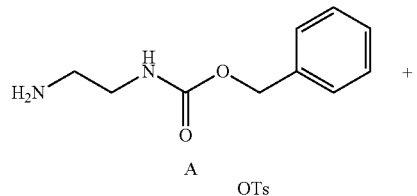

A

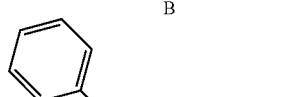

B

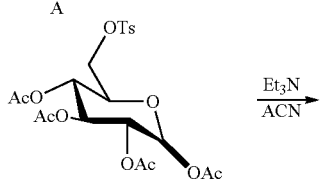

C

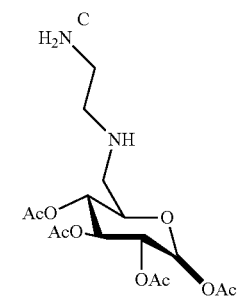

D

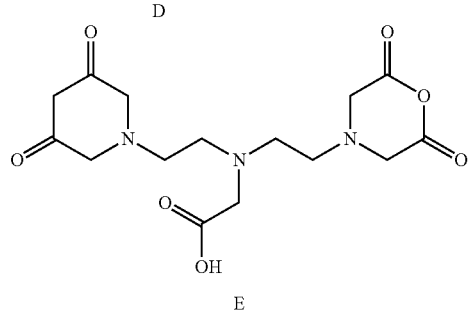

E

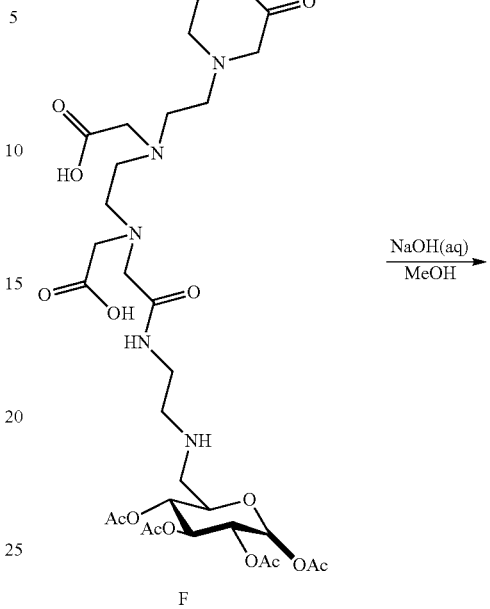

F

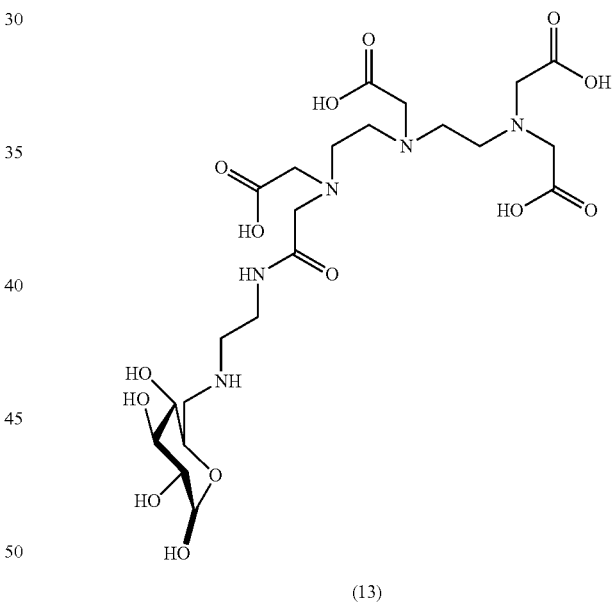

(13)

Mono(carbobenzoxy)ethylenediamine (A) may be monoalkylated with 6-tosyl-2,3,4,5-tetra-O-acetyl glucose (B) under dilute conditions with an organic base such as triethylamine. Following hydrogenolysis, to unmask the primary amine (D), and acetylation with an excess of DTPA-bis(anhydride) (E), to give the mono-acylate (F), the protected intermediate may be purified by reverse phase chromatography. Finally, saponification with sodium hydroxide and aqueous methanol, will provide the free glucosamine-DTPA (13).

Having described the invention in detail, it will be apparent that modifications and variations are possible without departing from the scope of the invention defined in the appended claims.

What is claimed is:

1. A metallopharmaceutical glucose, mannose, or galactose derivative compound of the formula:

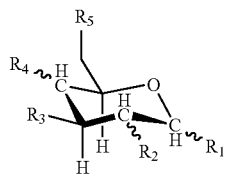

wherein:

$R_1$, $R_2$, $R_3$, and $R_4$ are independently hydrogen, hydroxyl, halogen, alkyl, carboxyl, or haloalkyl;

$R_5$ is a metal containing moiety of formula —$R_6$—$R_7R_8$ in which $R_6$ is a linker, $R_7$ comprises a metal coordinating moiety, and $R_8$ comprises one or more metal ions, wherein $R_6$ is

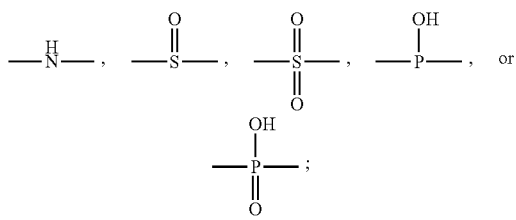

and $R_7$ is 1,4,7,10-tetraazacyclododecane-N,N',N'',N'''-tetraacetic acid (DOTA), diethylenetriaminepentaacetic anhydride (DTPA), or iminodiacetic acid (IDA).

2. The compound of claim 1, wherein $R_6$ is —NH—.

3. The compound of claim 1, wherein $R_1$, $R_2$, $R_3$, and $R_4$ are hydroxyl.

4. The compound of claim 1, wherein the compound comprises glucose.

5. The compound of claim 1, wherein $R_8$ is Lutetium, $^{177}$Lutetium, Yttrium, $^{86}$Yttrium, $^{90}$Yttrium, Indium, $^{111}$Indium, $^{113m}$Indium, Technetium, $^{98}$Technetium, $^{99m}$Technetium, Rhenium, $^{186}$Rhenium, $^{188}$Rhenium, Gallium, $^{67}$Gallium, $^{68}$Gallium, Copper, $^{62}$Copper, $^{64}$Copper, $^{67}$Copper, Gadolinium, $^{153}$Gadolinium, Dysprosium, $^{165}$Dysprosium, $^{166}$Dysprosium, Holmium, $^{166}$Holmium, Europium, $^{169}$Europium, Samarium, $^{153}$Samarium, Palladium, $^{103}$Palladium, Promethium, $^{149}$Promethium, Thulium, $^{170}$Thulium, Bismuth, $^{212}$Bismuth, Arsenic, or $^{211}$Arsenic.

6. The compound of claim 1, wherein $R_8$ is $^{177}$Lutetium, $^{86}$Yttrium, $^{90}$Yttrium, $^{111}$Indium, $^{113m}$Indium, $^{98}$Technetium, $^{99m}$Technetium, $^{186}$Rhenium, or $^{188}$Rhenium.

7. The compound of claim 4, wherein $R_1$, $R_2$, $R_3$, and $R_4$ are hydroxyl.

8. The compound of claim 7, wherein $R_6$ is —NH—.

9. The compound of claim 8, wherein $R_8$ is $^{177}$Lutetium, $^{86}$Yttrium, $^{90}$Yttrium, $^{111}$Indium, $^{113m}$Indium, $^{98}$Technetium, $^{99m}$Technetium, $^{186}$Rhenium, or $^{188}$Rhenium.

10. The compound of claim 8, wherein $R_8$ is $^{111}$Indium.

11. A pharmaceutical formulation comprising the compound of claim 1, wherein the formulation is suitable for administration as an imaging enhancing agent and the compound is present in an amount sufficient to enhance a single-photon emission computed tomography (SPECT) image, a computer assisted tomography (CAT) image, a magnetic resonance spectroscopy (MRS) image, a magnetic resonance imaging (MRI) image, a positron emission tomography (PET) image, a fluorescence image (FI), or an x-ray (XR) image.

12. The formulation of claim 11, wherein from about 1 microgram to about 50 micrograms of the compound are present.

* * * * *